US012366637B2

(12) United States Patent
Schipper et al.

(10) Patent No.: US 12,366,637 B2
(45) Date of Patent: Jul. 22, 2025

(54) ACTIVE TARGETS FOR TRACKING, AND METHODS FOR ASSEMBLING AND USING THE SAME

(71) Applicant: INTELLIJOINT SURGICAL INC., Kitchener (CA)

(72) Inventors: Joseph Arthur Schipper, Kitchener (CA); Ryan Visee, Mississauga (CA); Andre Novomir Hladio, Waterloo (CA)

(73) Assignee: Intellijoint Surgical Inc., Kitchener (CA)

( * ) Notice: Subject to any disclaimer, the term of this patent is extended or adjusted under 35 U.S.C. 154(b) by 837 days.

(21) Appl. No.: 17/666,849

(22) Filed: Feb. 8, 2022

(65) Prior Publication Data

US 2022/0252699 A1 Aug. 11, 2022

Related U.S. Application Data

(60) Provisional application No. 63/147,000, filed on Feb. 8, 2021.

(51) Int. Cl.
*G01S 7/481* (2006.01)
*G01S 7/484* (2006.01)
*G01S 17/46* (2006.01)

(52) U.S. Cl.
CPC .......... *G01S 7/4815* (2013.01); *G01S 7/4813* (2013.01); *G01S 7/484* (2013.01); *G01S 17/46* (2013.01)

(58) Field of Classification Search
CPC ............ A61B 2034/2055; A61B 34/20; A61B 2034/2046
See application file for complete search history.

(56) References Cited

U.S. PATENT DOCUMENTS

2017/0027447 A1\* 2/2017 Sutin ....................... G01J 3/108
2021/0186355 A1\* 6/2021 Ben-Yishai ............ A61B 34/10

\* cited by examiner

*Primary Examiner* — Gerald Johnson

(57) ABSTRACT

Described are targets for use in optical tracking, as well as related methods. A target comprises a plurality of light dispersers, optically coupled to at least one light source. The light dispersers are illuminated for detection and tracking by a tracking system. In some implementations, the at least one light source is optically coupled to the plurality of light dispersers by a plurality of light directors. In other implementations, the at least one light source includes a plurality of light sources positioned within or proximate to the plurality of dispersers. In some implementations, dispersers are lenses; in some implementations, dispersers are light scattering elements. Targets include or are coupled to a power source. In some implementations, targets include additional electrical components which utilize power from the power source.

20 Claims, 4 Drawing Sheets

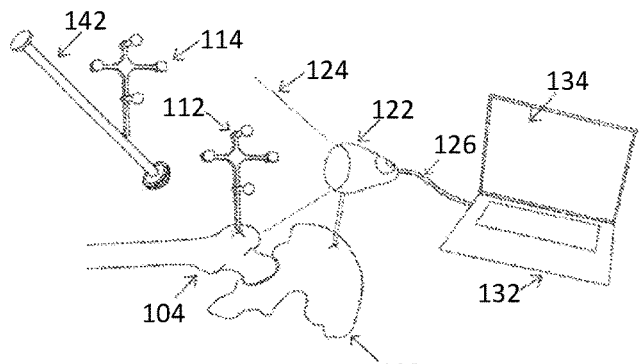
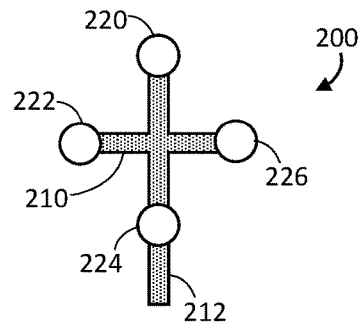
Figure 1
Figure 2A
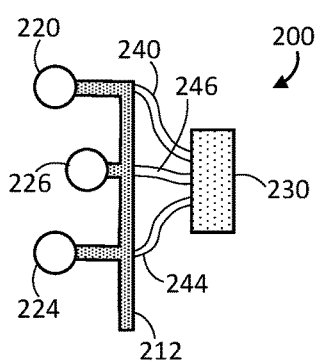
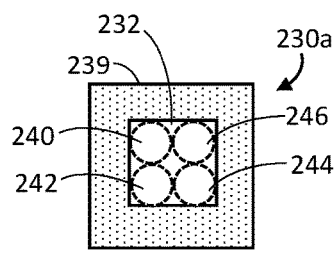
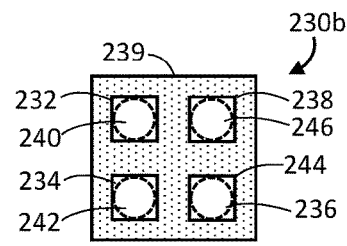
Figure 2B
Figure 2C
Figure 2D
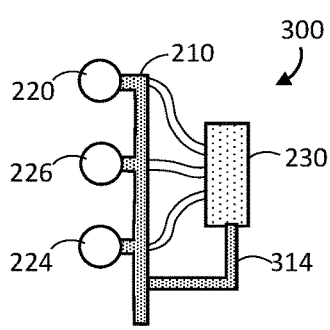
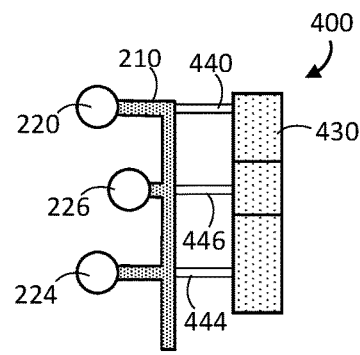
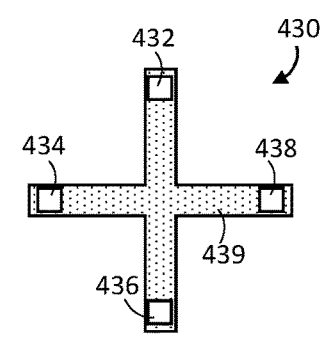
Figure 3
Figure 4A
Figure 4B

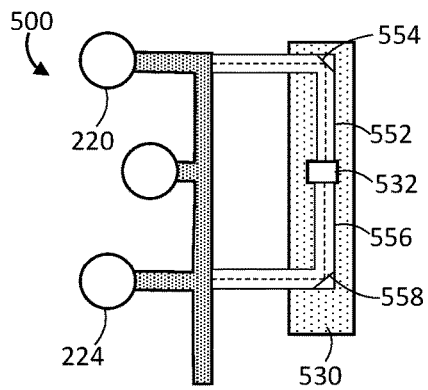
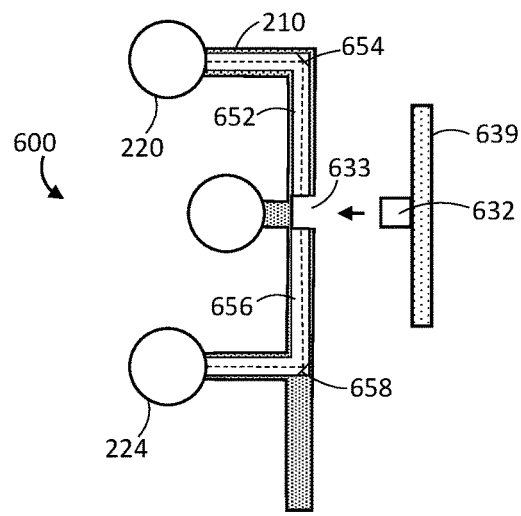
Figure 5
Figure 6
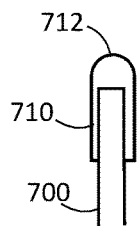
Figure 7A
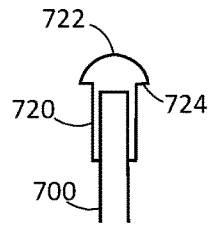
Figure 7B
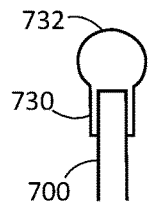
Figure 7C
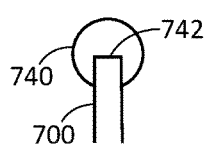
Figure 7D
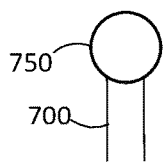
Figure 7E
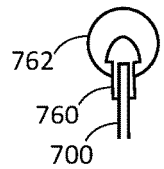
Figure 7F
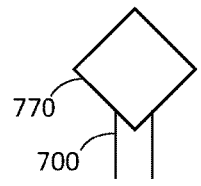
Figure 7G
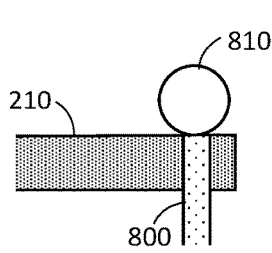
Figure 8A
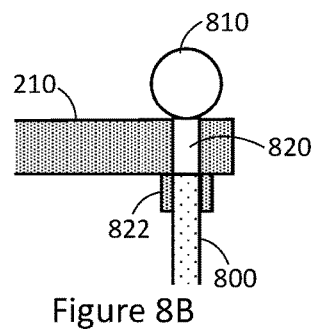
Figure 8B
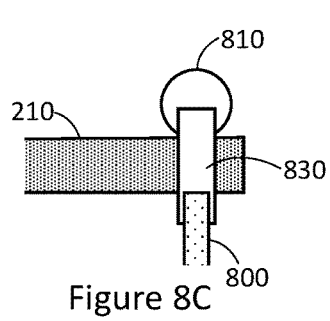
Figure 8C

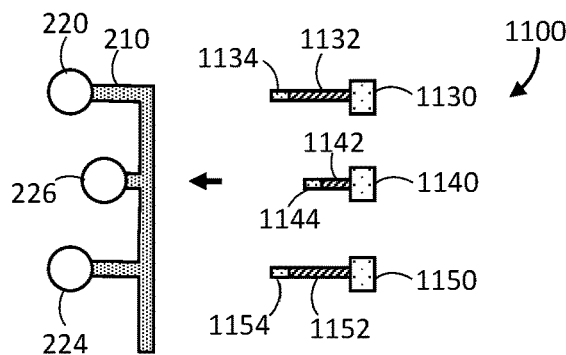
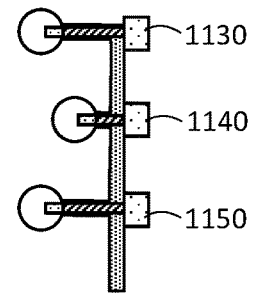
Figure 11A         Figure 11B
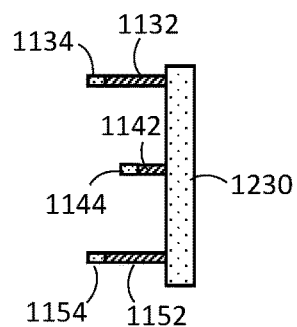
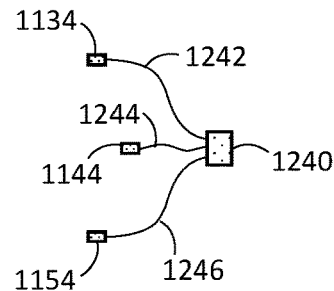
Figure 12A         Figure 12B
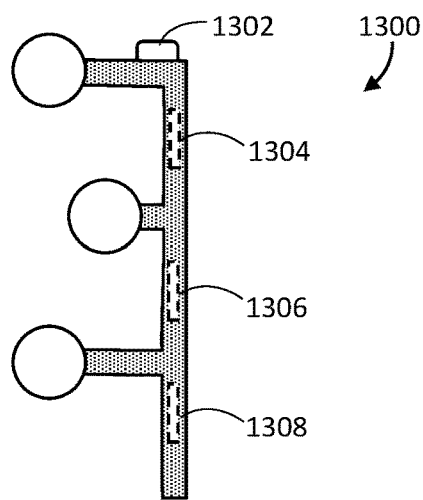
Figure 13

ACTIVE TARGETS FOR TRACKING, AND METHODS FOR ASSEMBLING AND USING THE SAME

CROSS-REFERENCE

This application claims the benefit of U.S. Provisional Application No. 63/147,000, filed Feb. 8, 2021, the entire contents of which are incorporated herein by reference.

FIELD OF THE INVENTION

The present disclosure relates to surgical tracking, and in particular relates to targets used in tracking, as well as methods for assembling and using such targets.

BACKGROUND

During a procedure, such as a surgical procedure, it can be desirable to register, detect, localize, and/or track various elements. Such elements include, for example, anatomy of a patient, or tools used during the surgery. Such tracking entails positioning a target having predetermined geometry on the element to be tracked, capturing image data representing the target, and determining a pose (position and orientation) of the target, or of the element relative to the target by a tracking system.

Existing targets rely on external light sources, and/or are susceptible to tracking difficulties when soiled.

The targets and methods described herein are not limited to surgical applications, but rather can be used in any appropriate application.

SUMMARY

Described are targets for use in optical tracking, as well as related methods. A target comprises a plurality of light dispersers, optically coupled to at least one light source. The light dispersers are illuminated for detection and tracking by a tracking system. In some implementations, the at least one light source is optically coupled to the plurality of light dispersers by a plurality of light directors. In other implementations, the at least one light source includes a plurality of light sources positioned within or proximate to the plurality of dispersers. In some implementations, dispersers are lenses; in some implementations, dispersers are light scattering elements. Targets include or are coupled to a power source. In some implementations, targets include additional electrical components which utilize power from the power source.

According to a broad aspect, the present disclosure describes a kit for use as a target in optical tracking when assembled, the kit comprising: a first support body; a plurality of light dispersers to be coupled to the first support body in a pattern identifiable by a tracking system; at least one light source to be coupled indirectly to the plurality of light dispersers, the at least one light source to be spatially separated from the plurality of light dispersers when the kit is assembled; a plurality of light directors, each light director to direct light from the at least one light source to a respective one of the light dispersers.

According to another broad aspect, the present disclosure describes a kit for use as a target in optical tracking when assembled, the kit comprising: a first support body; a plurality of light dispersers to be coupled to the first support body in a pattern identifiable by a tracking system; a plurality of light sources, each respective light source to be removably positioned in an interior volume of or proximate to a respective disperser.

According to yet another broad aspect, the present disclosure describes a kit for use as a target in optical tracking when assembled, the kit comprising: a first support body; at least one secondary support body to be coupled to the first support body; at least one light source coupled to the at least one secondary support body; a plurality of light dispersers to be coupled to the first support body in a pattern identifiable by a tracking system, each of the plurality of light dispersers to receive light from at least one of the at least one light source, and to disperse the received light.

According to yet another broad aspect, the present disclosure describes a light source unit for use in an optical tracking target having a plurality of light dispersers coupled to a first support body in a pattern identifiable by a tracking system, the light source unit comprising: a second support body couplable to the first support body; a plurality of light sources coupled to the second support body, each light source positioned and oriented to be received in an interior volume of or proximate to a respective disperser of the target when the second support body is coupled to the first support body.

According to yet another broad aspect, the present disclosure describes a light source unit for use in an optical tracking target having a plurality of light dispersers coupled to a first support body in a pattern identifiable by a tracking system, the light source unit comprising: a second support body; at least one light source coupled to the second support body; a plurality of coupling mechanisms for receiving a plurality of light directors proximate to the at least one light source, each light director to receive light from the at least one light source to provide the light to a respective disperser in the target.

According to yet another broad aspect, the present disclosure describes an optical tracking system comprising: a target, the target including: a first support body; at least one secondary support body coupled to the first support body; at least one light source coupled to the at least one secondary support body; and a plurality of light dispersers coupled to the first support body, each of the plurality of light dispersers to receive light from at least one of the at least one light source, and to disperse the received light; an image sensor to capture image data including at least one representation of the target and light from the plurality of light dispersers; and a processing unit to receive the image data from the image sensor and determine a pose of the target based on the captured image data.

According to yet another broad aspect, the present disclosure describes a method comprising: receiving a disperser unit, the disperser unit including a plurality of light dispersers coupled to a first support body in a pattern identifiable by a tracking system; and receiving a light source unit, the light source unit including at least one light source; coupling the at least one light source to the plurality of light dispersers by a plurality of light directors.

BRIEF DESCRIPTION OF THE FIGURES

FIG. 1 illustrates an exemplary scenario in which targets described herein can be used.

FIG. 2A is a front view of an exemplary target in accordance with an exemplary implementation. FIG. 2B is a side view of the target shown in FIG. 2A. FIGS. 2C and 2D are front views of exemplary light source units for use in the target of FIGS. 2A and 2B.

FIG. 3 is a side view of a target in accordance with another exemplary implementation.

FIG. 4A is a side view of a target in accordance with yet another exemplary implementation.

FIG. 4B is a front view of a light source unit for use in the target of FIG. 4A.

FIG. 5 is a side view of a target in accordance with yet another exemplary implementation.

FIG. 6 is a side view of a target in accordance with yet another exemplary implementation.

FIGS. 7A, 7B, 7C, 7D, 7E, 7F, and 7G are side cross-sectional views of dispersers for use in the targets described herein, in accordance with at least seven illustrated implementations.

FIGS. 8A, 8B, 8C, and 8D are side cross-sectional views of exemplary couplings between a light director and a disperser unit, in accordance with at least four illustrated implementations.

FIGS. 11A and 11B are side views of a target in accordance with yet another exemplary implementation. The target is shown having a disperser unit to which at least one light source unit is coupled.

FIGS. 12A and 12B are side views of alternate light source units for use in the disperser unit illustrated in FIG. 11A.

FIG. 13 is a side view which illustrates exemplary components which can be implemented in targets having a power source.

DETAILED DESCRIPTION

Figure 8D:
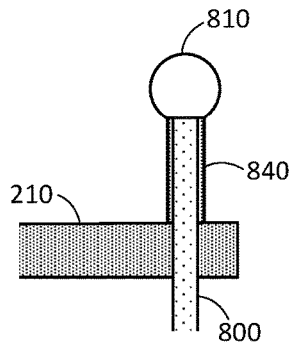

The description herein details several exemplary embodiments. One skilled in the art will appreciate that it is within the scope of the present disclosure to combine individual embodiments with other embodiments as appropriate.

FIG. 1 illustrates an exemplary scenario in which a surgical procedure is being performed. Any of the targets or tracking systems described herein can be used in the context described with reference to FIG. 1, and in the ways described with reference to FIG. 1.

In the example of FIG. 1, a total hip arthroplasty (THA) is being performed, but the discussion herein is applicable to any surgical procedure where a tracking system is used, or any appropriate procedure other than surgery. In FIG. 1, a patient's pelvis 102 and femur 104 are shown. A target 112 is positioned on (e.g. affixed to, mounted on, or touched against) femur 104. As examples, target 112 could include an extension with a tip for probing the femur; target 112 could be coupled to the femur by at least one of a pin or screw; or target 112 could be removably coupled to a mount (such as a magnetic mount) which in turn is coupled to the femur by at least one of a pin or screw. An image sensor 122 is positioned on pelvis 102. Image sensor 122 can capture image data over a field of view 124. Image sensor 122 can communicate captured image data to computing device 132. Image sensor 122 is shown as being communicatively coupled to computing device 132 by wire 126, but wireless communication between image sensor 122 and computing device 132 is also possible. Further, it is also possible for image sensor 122 and computing device 132 to be a unified device. Computing device 132 can analyze the image data (for example by at least one processor in computing device 132), or computing device 132 can send the data to a remote device or cloud server for analysis, to detect target 112 and determine a pose (position and orientation) thereof. Pose can be position or orientation in three-dimensional space, though in certain applications pose can be position and orientation in two-dimensional space. Further, based on the pose and pre-determined geometry of target 112, computing device 132 can also determine a pose of elements which target 112 is positioned on. In the example of FIG. 1, image sensor 122 can be affixed to pelvis 102, and target 112 can be affixed to femur 104. Consequently, movement of target 112 relative to image sensor 122 can correspond to movement of the femur 104 relative to pelvis 104. In this context, "tracking" an element can entail continuously, regularly, or intermittently determining a pose of the element.

FIG. 1 also illustrates target 114 positioned on a tool 142. In the case of FIG. 1, tool 142 is a cup impactor for implanting a prosthetic hip cup during THA, but target 114 can be positioned on any appropriate tool. As examples, target 114 could include an extension with a tip for probing the tool; target 114 could be coupled to the tool by clips or fasteners; or target 114 could be removably coupled to the tool by magnetism (directly, or indirectly via a magnetic mount secured to the tool). Image sensor 122 can capture image data including target 114, which can subsequently be analyzed by computing device 132 (or a remote analysis device as mentioned above) to determine pose information of tool 142. Target 114 can be identical to target 112, or target 114 and target 112 could be different (for example by having different geometry from each other). In some implementations, target 112 could be removably positioned on a base mounted to femur 104, such that target 112 can be removed from and replaced on femur 104 without affecting the positioning of target 112 when positioned on femur 104. In such cases, target 112 can be removed from the base, and positioned on other elements (such as tool 142), such that multiple tracking operations can be achieved with a single target. In such implementations, the functionality of target 114 could be achieved with target 112.

Information based on the pose of an element of interest can be presented by display 134 of computing device 132 (or another device). This information can provide helpful or critical information to the surgeon. Further, other output means can also be used, such as audio output like speakers.

In order to accurately determine the pose of the anatomy (e.g. pelvis 102, femur 104) or the tool 142, registration steps can be performed to determine the geometry of the anatomy/tool relative to a target. As non-limiting examples, steps such as probing the element with a target, moving the element with the target in the field of view of the image sensor, or registering additional information such as acceleration or gravity data using an accelerometer in the sensor 122 and/or target 112 or 114, can be performed.

FIG. 1 shows exemplary anatomy of pelvis 102 and femur 104. However, any appropriate anatomy can be tracked, including for example leg, arm, torso, head, back, or chest anatomy, including bones therein. As mentioned above, the targets discussed herein can also be used in non-surgical applications.

Throughout this disclosure, reference is made to a "tracking system". Such a tracking system can refer to a device such as computing device 132, or any other appropriate device capable of processing, which can receive data representing a target, and determining a pose of the target or pose of an element in contact with the target. Broadly, a tracking system can also include an image sensor and a target.

This disclosure describes a number of "active targets". In this context, "active" refers to the ability of the target to emit light. In contrast, a "passive" target is a target which reflects, disperses, or diffuses light from another light source.

FIG. 2A is a front view of an exemplary target 200. FIG. 2B is a side view of the target 200. Target 200 includes a support body 210, coupled to four light dispersers 220, 222, 224, and 226. Fewer or more dispersers could be included, as appropriate for a given application. Support unit 210, together with dispersers 220, 222, 224, and 226, can be referred to as a "disperser unit". Throughout this disclosure, an element comprising dispersers coupled to a support body can be referred to as a "disperser unit". Dispersers 220, 222, 224, and 226 are shown attached to support unit 210. In some implementations, this attachment can be permanent, such as with soldering, permanent adhesive, or other fasteners. In other implementations, this attachment can be removable, such as with clips, temporary adhesive, or other fasteners. Further, the disperser unit can be provided to a user as separate components to be assembled; that is support body 210 and dispersers 220, 222, 224, and 226 can be provided with coupling mechanisms such as adhesive, clips, mechanical threads, or other fasteners such that a user (e.g. surgeon or assistant) assembles the disperser unit by attaching the dispersers to the support body.

Target 200 also includes at least one light source unit 230 (FIG. 2B), which is to provide light to the dispersers 220, 222, 224, and 226. In target 200, the disperser unit and the light source unit 230 can be provided as separate components of a kit, where the disperser unit and the light source unit 230 are configured to be coupled together. This applies to all of the targets described herein: the targets are provided as kits having a diffuser unit and a light source unit which are couplable to form the target. The diffuser unit and the light source unit do not necessarily have to be provided together in one package, but rather can be provided separately, such that either component can be replaced as needed, as discussed in detail later. In target 200, light source unit 230 is spatially separated from dispersers 220, 222, 224, and 226 when coupled to the disperser unit to form the assembled target. Light directors 240, 244, and 246 direct the light from the light source unit 230 to dispersers 220, 224, and 226, respectively. A fourth light director is included to direct light from light source unit 230 to disperser 222, but is occluded in FIGS. 2A and 2B. That is, a respective light director can direct light from light source unit 230 to each disperser. In this sense, light sources on light source unit 230 are indirectly coupled to the plurality of light dispersers 220, 222, 224, and 226. Each disperser will receive the light, and disperse the light away from the target. Exemplary dispersers include diffusers or lenses which spread light out or introduce randomness in the direction of light from the dispersers. A tracking system which views the target will receive light from the dispersers, and can determine a pose of the target based on the relative position of each of the dispersers. In the exemplary target of FIGS. 2A and 2B, a tracking system will view four spheres of light (the dispersers), and determine the pose of the target based on the relative orientation of the four spheres of light compared to a known geometry of the target.

The dispersers herein receive light from a light source, and disperse the light over a broad angular range. A tracking system can receive the dispersed light and determine a position of the disperser. By virtue of dispersion of light, the disperser can be visible to the tracking system even at a wide viewing angle. This contrasts with for example a non-dispersive light source which outputs highly directional light (i.e. light emitted over a smaller angular range), where the light source will only be visible to the tracking system if an image sensor of the tracking system is positioned in the path of the directional light. To achieve dispersion, exemplary dispersers include diverging lens structures, such as a convex lens. In some implementations, dispersers can include light scattering material or mechanisms, such as surface roughness or material variability. As one example, a disperser could be made of roughened polycarbonate. Such polycarbonate can be relatively, moderately, or partially transparent, allowing light to pass therethrough with minimal influence; but by roughening the surface of the polycarbonate, light incident thereon is scattered, such that light entering the polycarbonate will be scattered in many directions into the polycarbonate, and light exiting the polycarbonate will be further scattered in many directions upon exit. This scattering of light introduces variation and randomness in the direction of light, thereby producing diffuse light. In some implementations, a single disperser could include both diverging lens mechanics and scattering mechanics. Exemplary dispersers are discussed later with reference to FIGS. 7A-7G. In some implementations, engineered diffusers could be used, which output diffuse light from a specified area of a diffuser. In some implementations, such engineered diffusers have a patterned surface which diffuses light which passes through specific areas of the diffuser, so as to produce identifiable shapes of diffuse light. For example, an engineered diffuser can be designed to output diffuse light from a square shape, circular shape, or line shape, regardless of the shape of the diffuser itself.

The light directors herein serve to direct light from a light source to a disperser, with minimal loss of light therebetween. In some implementations, a light director is a light pipe or an optical fiber which guides light from the light source using total internal reflection. In other implementations, a light director is a shielding which surrounds a light path and prevents escaping of light from said path (e.g., a hollow cylindrical shield which encircles a straight light path). In other implementations, a light director is a reflective surface or series of reflective surfaces which direct light from a light source along a desired path. In yet other implementations, a light director is a waveguide which directs light over a plane or line using total internal reflection. Any of these implementations could be combined as appropriate for a given application. For example, an optical fiber could be surrounded with a coating or shielding to concurrently direct light via the fiber, and prevent escape of stray light via the coating or shielding. Stray light can potentially interfere with detectability of dispersers, so it is preferable to prevent such stray light from escaping to the environment where it may be detected by a tracking system. Further, in some implementations, it is desirable to prevent stray light from escaping into other parts of the target which are not intended. For example, in some implementations, light provided to the dispersers can be strobed (flashed or pulsed) at different times or frequencies, which can provide more information about the target, such as a target identification to differentiate between a plurality of targets. In such implementations, if light intended for one disperser escapes and illuminates another disperser, this could comprise a detected strobing pattern, and could cause tracking errors or target misidentification. In some implementations, light can enter into a target body from other sources (such as an overhead light), which can improperly illuminate dispersers. Shielding or similar can prevent such light from entering the target body.

To achieve tracking, the light dispersers are positioned in a pattern which is identifiable by the tracking system. In particular, the light dispersers can be positioned relative to each other according to a pre-defined geometry which enables the tracking system to identify a pose of the target based on the relative position of the dispersers as viewed by the tracking system. The exemplary target 200 has a cross shape as shown in FIG. 2A, but any appropriate shape could be used.

To improve detection, the light source unit 230 can emit light having a wavelength in a waveband which an image sensor in the tracking system is sensitive to or is tuned to. For example, light source unit 230 can emit infrared (IR) light, to be received by an infrared image sensor of a tracking system. Other wavelengths of light are possible.

Target 200 is shown as including an optional extension 212 coupled to support body 210. A similar extension can be included in any of the targets described herein. In an example, extension 212 is integrally formed with support body 210. In an alternative example, extension 212 is a separate component which is coupled to support body 210, for example, by fasteners such as clips, screws, bolts, pins, threads, or adhesive, or by processes such as welding, melting, or soldering. Such coupling could also be removable, such as a magnetic coupling. Any appropriate coupling between the extension 212 and the support body 210 could be used. Extension 212 advantageously provides a region or point of the target distal from the dispersers which can be used to track elements that would otherwise occlude the dispersers. In an exemplary use case, a bone in an incision is to be tracked, but the tissue surrounding the bone would occlude at least one disperser from view of a tracking system if the target were to be inserted into the incision. In such a case, extension 212 is included in the target, and extension 212 is inserted into the incision to contact or couple to the bone. In this way, the dispersers can be positioned external to the incision, such that they are fully visible to the tracking system. As an example for how target 200 (or any of the targets discussed herein) can be positioned for tracking an object (e.g. bone or surgical tool): extension 212 can have a tip distal from target 200 suitable for probing the object. As further examples, extension 212 could be adapted to couple to the object by at least one of a pin, screw, clip, or other fastener; extension 212 could be adapted to couple directly to a ferromagnetic object such as a surgical tool by magnetic force; or extension 212 could be adapted to removably couple to a mount (such as a magnetic mount) which in turn is adapted to couple to the object such as by at least one of a pin, screw, clip, or other fastener. Couplings via extension 212 are preferably at an end of extension 212 distal from support body 210. Similar coupling mechanisms could be implemented at other regions of target 200 even if target 200 does not include extension 212

FIG. 2C is a top view of an exemplary light source unit 230a, for use as light source unit 230 in target 200. Light source unit 230a includes a support body 239 (for example a substrate), having one light source 232 positioned thereon. Light source 232 (or any light source herein) could, for example, be a light emitting diode (LED) or other device such as a lamp that is a source of light to emit optical (electromagnetic) radiation, which may, but need not be, in the visible spectrum of light. As noted, the light emitted may be IR light. A first end of light directors 240, 242, 244, and 246 is coupled to light source unit 230a, positioned proximate light source 232 to receive light therefrom (for example as discussed later with reference to FIGS. 9A and 9B). A second end of each of light directors 240, 242, 244, and 246 is coupled to a respective disperser (directly or indirectly through support body 210, as will be discussed later with reference to FIG. 8A-8D), to provide light from light source 232 to each of the dispersers. In particular, light director 240 provides light to disperser 220, light director 242 provides light to disperser 222, light director 244 provides light to disperser 224, and light director 246 provides light to disperser 226, from light source 232.

Light source unit 230a advantageously provides light to all of the dispersers with a single light source, which is power and space efficient. However, positioning each of the light directors to direct similar amounts of light to each of the dispersers can be challenging, and the dispersers may thus be unevenly lit. FIG. 2D is a top view of another exemplary light source unit 230b, for use as light source unit 230 in target 200. Light source unit 230b includes a support body 239 (for example a substrate), having four light sources 232, 234, 236, and 238 positioned thereon. Fewer or more light sources could be included as appropriate for a given application; generally it is preferable for an individual light source (or even plurality of light sources) to be included for each disperser to be illuminated. Light sources 232, 234, 236, and 238 could for example be LEDs. A first end of light director 240 is coupled to light source unit 230b, positioned proximate light source 232 to receive light therefrom. A second end of light director 240 is coupled to disperser 220 (directly or indirectly), to provide light from light source 232 to disperser 220. A first end of light director 242 is coupled to light source unit 230b, positioned proximate light source 234 to receive light therefrom. A second end of light director 242 is coupled to disperser 222 (directly or indirectly), to provide light from light source 234 to disperser 222. A first end of light director 244 is coupled to light source unit 230b, positioned proximate light source 236 to receive light therefrom. A second end of light director 244 is coupled to disperser 224 (directly or indirectly), to provide light from light source 236 to disperser 224. A first end of light director 246 is coupled to light source unit 230b, positioned proximate light source 238 to receive light therefrom. A second end of light director 246 is coupled to disperser 226 (directly or indirectly), to provide light from light source 238 to disperser 226. In this way, each disperser is coupled to a respective light source by a light director, such that each light source illuminates a respective disperser. Such an implementation improves consistency of illumination of the dispersers.

Coupling between light directors and any of the support body 210; dispersers 220, 222, 224, and 226; and light source unit 230 can be permanent, or can be removable. In the case of removable couplings, light source unit 230 can be considered as an attachment separate from the support body 210 of target 200. Exemplary couplings are discussed in detail later with reference to FIGS. 7A-7G, 8A-8D, 9A and 9B.

To power the at least one light source in any of the light source units discussed herein, a target includes or is coupled to a power source. As examples, a target can carry a battery, or can be coupled to a remote power source by a wire. In implementations where a light source unit is removably coupled to a disperser unit, the light source unit preferably includes or is coupled to the power source. However, in some implementations it is possible for the disperser unit to include or be coupled to the power source, with an electrical coupling to the light sources on the light source unit.

Target 200 is shown with the plurality of dispersers being positioned in different planes. In particular, in FIG. 2B dispersers 220 and 224 are shown as being positioned in a first plane, whereas disperser 226 is positioned in a different second plane (along with disperser 222 occluded from view in FIG. 2B). Such positioning advantageously improves three-dimensional trackability of the target, but is not required. FIG. 3 is a side view of an exemplary target 300 which is similar to target 200. Unless context dictates otherwise, description of target 200 is applicable to target 300, and vice-versa. One difference between target 300 in FIG. 3 and target 200 in FIG. 2B is that in target 300, dispersers 220, 222, 224, and 226 are positioned in a common plane.

Another difference between target 300 in FIG. 3 and target 200 in FIG. 2B is that target 300 is shown as including a coupling member 314. Coupling member 314 couples support body 210 to light source unit 230. Coupling member 314 is an optional component which can provide extra strength and/or rigidity to the coupling between support body 210 and light source unit 230. If light directors 240, 242, 244, and 246 are themselves strong and stable enough to secure light source element 230 to support body 210 without breaking, coupling member 314 is unnecessary. The light directors themselves could be reinforced to this end. Additional coupling members could optionally be included for further strength and rigidity. In some implementations coupling member 314 is permanently attached to both light source unit 230 and to support body 210. In such implementations, light directors 240, 242, 244, and 246 may be removable from light source unit 230 and support body 210 for autoclaving of the target. In other implementations, attachment between coupling member 314 and at least one or both of support body 210 and light source unit 230 is non-permanent, such that support body 210 and light source unit 230 are separable for autoclaving or replacement or either component.

Coupling member 314 need not be a rigid element. In an exemplary alternative, coupling member 314 is a flexible strap which secures light source unit 230 to support body 210.

In some exemplary implementations, light source unit 230 is removably coupled to support body 210 by magnetic force. For example, one of support body 210 and light source unit 230 can carry at least one magnet, which is magnetically attracted to another at least one magnet or ferromagnetic material in the other of support body 210 and light source unit 230. In some implementations, support body 210 and/or light source unit 230 can be magnetically coupled to coupling member 314.

Light directors 240, 242, 244, and 246 are shown in FIGS. 2B and 3 as being curved optical fibers or pipes. However, alternate structures are possible. FIGS. 4A and 4B illustrate one exemplary structure.

FIG. 4A is a side view of a target 400 which is similar to target 200. Unless context dictates otherwise, description of target 200 is applicable to target 400, and vice-versa. One difference between target 200 and target 400 is that in target 400 the light directors are straight, as opposed to curved. FIG. 4B is a front view of light source unit 430, which is shown coupled to support body 210 in FIG. 4A. Light source unit 430 (similar to light source unit 230) has light sources 432, 434, 436, and 438 positioned on a support body 439 in positions which align with respective dispersers 220, 222, 224, and 226 when light source unit 430 is coupled to support body 210. That is, light source unit 430 has a cross shape which is similar to the cross shape of a disperser body of target 400. In this way, the light directors (440, 444, and 446 visible in FIG. 4A) can be straight. Straight light directors have a number of advantages, including less light loss. Additionally, straight light directors are more easily reinforced than curved directors, reducing the need for additional coupling members like coupling member 314. Further, light source unit 430 can be positioned closer to support body 210 with straight redirectors (or even butted thereagainst), since the path of light is more direct, and there is no need to design curve paths which stay within limited curve angles (to avoid outcoupling of light from a curved director, or breaking of the director).

FIG. 5 is a side view of a target 500 which is similar to target 400. Unless context dictates otherwise, description of target 400 is applicable to target 500, and vice-versa. One difference between target 400 and target 500 is that in target 500, light source unit 530 has light directors therein, to direct light from at least one light source 532 to positions which align with positions of respective dispersers before directing the light towards the dispersers. In particular, light director 552 directs light from light source 532 towards an upper periphery of light source unit 530, before directing the light towards disperser 220. Similarly, light director 556 directs light from light source 532 towards a lower periphery of light source unit 530, before directing the light towards disperser 224. In the example of FIG. 5, a mirror 554 directs the light towards disperser 220, and a mirror 558 directs the light towards disperser 224. However, alternative directors could be used, for example if light directors 552 and 556 are transparent light guides, exterior surfaces thereof could be beveled and silvered at points 554 and 558. Additional light directors are included to direct light to each of the other dispersers, but are not shown in FIG. 5 to reduce clutter.

FIG. 6 is a side view of a target 600 which is similar to target 500. Unless context dictates otherwise, description of target 500 is applicable to target 600, and vice-versa. One difference between target 500 and target 600 is that in target 600, light directors can be built into the support body 210. In particular, light directors 652 and 656 are provided which direct light towards a periphery of the target, before directing the light towards dispersers 220 and 224 by mirrors 654 and 658 (similarly to light directors 552 and 556, and mirrors 554 and 558 discussed regarding FIG. 5). At least one recess 633 is provided, into which at least one light source 632 is inserted, such that light from light source 632 is received in light directors 652 and 656. Light source 632 is carried by support body 639, which can be coupled to support body 210, to secure light source 632 in position. As similarly discussed regarding FIG. 5, additional light directors are included to direct light to each of the other dispersers, but are not shown in FIG. 6 to reduce clutter.

In FIG. 5, a single light source 532 is illustrated, and in FIG. 6 a single light source 632 is illustrated. More light sources could be included as appropriate for a given application. For example, a plurality of light sources could be included, each light source to output light into a respective light director, to illuminate a respective disperser.

FIGS. 7A, 7B, 7C, 7D, 7E, 7F, and 7G are side cross-sectional views of exemplary dispersers which can be used as the dispersers in any of the targets discussed herein.

FIG. 7A illustrates a light director 700 having a cap 710 positioned at an end thereof, where cap 710 acts as a disperser. Cap 710 (and any of the other caps discussed herein) is formed of a transparent or translucent material. Cap 710 comprises a lens surface 712. In the example of FIG. 7A, lens surface 712 is a convex, partially spherical shape or dome shape, to diverge light which passes therethrough from light director 700. Cap 710 is shown as a separately manufactured component from light director 700, which is coupled thereto; for example, light director 700 can be inserted into a recess in cap 710 and held there by a friction fit or adhesive. In this way, different caps can be interchanged to achieve different dispersive properties. Further, cap 710 could be secured to a support body of a target (such as support body 210 discussed above), and light director 700 could be removably coupled to cap 710. In this way, removable coupling between the light director and the support body/disperser is achieved. In alternative implementations, cap 710 is secured to light director 700, and cap 710 is removably couplable to support body 210. In some implementations, cap 710 could be permanently coupled to light director 700, or cap 710 could be integrally formed with light director 700.

FIG. 7B illustrates light director 700 having a cap 720 positioned at an end thereof, where cap 720 acts as a disperser. Cap 720 is similar to cap 710 discussed with reference to FIG. 7A, and discussion of cap 710 is applicable to cap 720 unless context dictates otherwise. One difference between cap 720 and cap 710 is that cap 720 flares out at an end thereof. That is, lens surface 722 extends beyond the main body of cap 720. Such flaring produces wider divergence of light through lens surface 722 from light director 700. Further, such flaring also provides a surface 724 which can be used for securing cap 720 to support body 210 (or other components) via clips, adhesive, fasteners, or any other appropriate coupling mechanisms.

FIG. 7C illustrates light director 700 having a cap 730 positioned at an end thereof, where cap 730 acts as a disperser. Cap 730 is similar to caps 710 and 720 discussed with reference to FIGS. 7A and 7B, and discussion of caps 710 and 720 is applicable to cap 730 unless context dictates otherwise. One difference between cap 730 and caps 710 and 720 is that cap 730 has a spherical shape 732 at an end thereof, with a stem having a recess in which light director 700 is received. Such a spherical shape 732 can diverge light from light director 700 similar to lens surfaces 712 and 722, but in a wider spherical pattern. Additionally, when viewed by a tracking system, a spherically shaped disperser has the same centroid regardless of viewing angle, and thus calculations of pose based on spherical dispersers are less processor intensive and more efficient than for other shapes of disperser.

FIG. 7D illustrates light director 700 having a cap 740 positioned at an end thereof, where cap 740 acts as a disperser. Cap 740 is similar to cap 730 discussed with reference to FIG. 7C, and discussion of cap 730 is applicable to cap 740 unless context dictates otherwise. One difference between cap 740 and cap 730 is that cap 740 has a recess 742 within the sphere shape to receive an end of light director 700. That is, a portion of light director 700 is inserted into the sphere of cap 740, and can be held in place with friction, adhesive, clips, or other fasteners.

FIG. 7E illustrates light director 700 having a spherical disperser 750 positioned at an end thereof. disperser 750 is similar to caps 730 and 740 discussed with reference to FIGS. 7C and 7D, and discussion of caps 730 and 740 is applicable to disperser 750 unless context dictates otherwise. One difference between disperser 750 and caps 730 and 740 is that disperser 750 is butted against an end of light director 700, instead of the disperser receiving light director 700 therein. In this way, light from light director 700 is received on an external surface of disperser 750, incoupled into an interior volume of disperser 750, and subsequently outcoupled through the remaining external surfaces of disperser 750. Such an implementation increases the surface boundaries and total volume through which light is dispersed, resulting in more even dispersion (for example if the surface of the disperser is roughened as in a diffuser). In some implementations, light director 700 need not physically contact disperser 750, but rather can direct light onto disperser 750 across a gap.

FIG. 7F illustrates light director 700 having a cap 760 positioned at an end thereof, with a diffuser 762 positioned around cap 760. Cap 760 is similar to caps 710, 720, and 730 discussed with reference to FIGS. 7A, 7B, and 7C, and discussion of caps 710, 720, and 730 is applicable to cap 760 unless context dictates otherwise. Diffuser 762 is similar to cap 740 discussed with reference to FIG. 7D, and discussion of cap 740 is applicable to diffuser 762 unless context dictates otherwise. The inclusion of both cap 760 and diffuser 762 provides enhanced diffusion of light from light director 700. For example, cap 760 is a lens which disperses/diverges light from light director 700; and diffuser 762 is formed of a scattering material which scatters the diverged light. The divergence and scattering together can evenly diffuse light. Further, in some implementations, cap 760 can be permanently coupled to (or integrally formed with) light director 700, such that features of cap 760 can be used for coupling to diffuser 762. In the example of FIG. 7F, flared surfaces of cap 760 (similar to flared surfaces 724 in FIG. 7B) can couple to diffuser 762 via clips, mating features of diffuser 762, or other fasteners.

FIG. 7G illustrates a light director 700 having a disperser 770 positioned at an end thereof. Disperser 770 is similar to cap 740 and disperser 750 in FIGS. 7D and 7E, and discussion of cap 740 and disperser 750 is applicable to disperser 770 unless context dictates otherwise. One difference between disperser 770 and cap 740 and disperser 750 is that disperser 770 is not spherically shaped. In the example of FIG. 7G, disperser 770 is shaped as a diamond. Such a non-spherical shape produces patterns in dispersed light, such as highlighted corners or edges. Such patterns are detectable by a tracking system, and can be used to determine a pose of a target having the disperser. For example, a target with a plurality of dispersers could have differently shaped dispersers, such that the orientation of the different disperser shapes indicates an orientation of the target. The diamond shape of FIG. 7G is merely exemplary, and any other appropriate shapes could be used. Further, any of the dispersers discussed herein could have non-spherical shapes as appropriate for a given application. In some implementations, patterns in dispersed light are achieved by masking certain areas of a disperser with opaque material. In an example, a disperser is formed as a diffuser comprising transparent or translucent polycarbonate, and has opaque portions, cladding, paint, or other material on a surface or surfaces thereof. Such opaque material defines a pattern in the uncovered diffuse material, which is detectable by a tracking system. As one example, a diffuser with a square profile has an opaque cross on a surface thereof, defining a pattern of diffusive corners uncovered. These corners are viewed and detected by a tracking system. As another example, polka-dot, checkered, or other distinct visual patterns which do not fundamentally change the perceived shape of a diffuser can be applied to the diffuser, which is useful for identifying the diffuser and/or the target on which the diffuser is positioned.

FIGS. 7A-7G illustrate exemplary dispersers (including caps which function as dispersers) which can be positioned on an end of a light director. In any of the targets discussed herein, a plurality of such dispersers or caps could be implemented, to provide a plurality of dispersers.

FIGS. 8A, 8B, 8C, and 8D are partial side cross-sectional views of exemplary couplings between a support body, disperser, and light director. That is, FIGS. 8A, 8B, 8C, and 8D illustrate exemplary couplings between disperser units and light directors. In each of FIGS. 8A, 8B, 8C, and 8D, only a single disperser and a portion of a support body are shown, but the illustrated couplings can be applied for a plurality of dispersers over a support body. Such couplings can be used in any of the targets discussed herein.

FIG. 8A illustrates support body 210, which receives an end of light director 800 through an opening therein, to position the end of light director 800 proximate a disperser 810. In this way, light from light director 800 is coupled directly into disperser 810. Light director 800 is secured either permanently or removably to support body 210 by, for example, a friction fit, adhesive, or other fasteners.

FIG. 8B illustrates support body 210, which receives an end of light director 800 proximate a surface thereof. Support body 210 has a passage 820 therethrough which receives light from light director 800, and provides the light to disperser 810. Light director 800 is secured either permanently or removably to support body 210 by coupling members 822, which can comprise friction fit members, clips, or other fastening members. Adhesive could optionally be further used. Passage 820 can be a hollow passage, or could have transparent material therein, such as an optical fiber or light guide.

FIG. 8C illustrates support body 210, which receives an end of light director 800 proximate a surface thereof. Support body 210 has a passage therethrough which receives a cap 830, which can be similar to caps 710, 720, 730, and 760 discussed with reference to FIGS. 7A, 7B, 7C, and 7F above. Cap 830 couples to an end of light director 800, extends through support body 210, and is positioned proximate to or partially within disperser 810, to direct light from light director 800 through support body 210 to disperser 810. In some implementations, cap 830 is permanently coupled to support body 210, and light director 800 is removably coupled to cap 830. In this way, light director 800 is removable from support body 210 by removal of light director 800 from cap 830. In other implementations, cap 830 is permanently coupled to light director 800, and removably coupled to support body 210. In this way, light director 800 is removable from support body 210 by removal of cap 830 from support body 210. In some implementations, cap 830 can be integrally formed with disperser 810, such that effectively disperser 810 includes an extension or sleeve which extends through the passage in support body 210. The couplings between support body 210, light director 800, disperser 810, and cap 830 can comprise friction fit, clips, adhesive, or other fasteners.

FIG. 8D illustrates support body 210 which has a post 840 coupled thereto (or integrated therewith), with disperser 810 coupled to an end of post 840 distal from support body 210. Support body 210 and post 840 receive an end of light director 800 through an opening therethrough, to position the end of light director 800 proximate a disperser 810. In this way, light from light director 800 is coupled directly into disperser 810. Light director 800 is secured either permanently or removably to support body 210 by, for example, a friction fit, adhesive, or other fasteners. In alternative implementations, light director 800 may not run all the way through support body 210 or post 840. For example, either or both of post 840 and support body 210 could have a passage therethrough, similar to passage 820 described with reference to FIG. 8B, such that light director 800 can provide light to the passage, which in turn directs the light to disperser 810. In another implementation, disperser 810 in FIG. 8C is positioned spatially separated from support body 210 by a gap, with cap 830 extending across said gap. In this way, cap 830 effectively serves a similar purpose to post 840 in FIG. 8D. In such an implementation, the portion of cap 830 extending across the gap can be shielded or masked to prevent light from escaping to the environment.

The dispersers in FIGS. 8A-8D are shown as having a circular profile. However, other disperser shapes are possible, such as those discussed with reference to FIGS. 7A-7G.

Figure 9A:
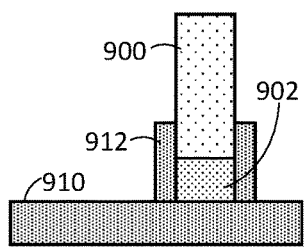
FIGS. 9A, 9B, and 9C are side cross-sectional views of exemplary couplings between a light director and a light source unit, in accordance with at least three illustrated implementations.
Figure 9B:
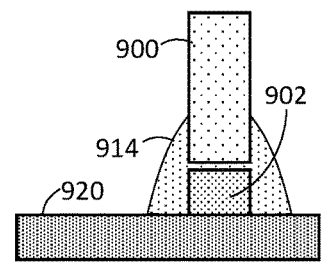
Figure 9C:
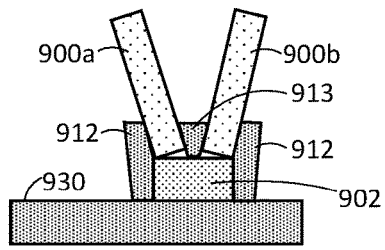

FIGS. 9A, 9B, and 9C are side cross-sectional views of exemplary couplings between a support body of a light source unit (for example support body 239 of light source unit 230, or support body 439 of light source unit 430), a light source, and a light director. In each of FIGS. 9A, 9B, and 9C, only a single light source and a portion of a support body are shown, but the illustrated couplings can be applied for a plurality of light sources over a support body. Such couplings can be used in any of the targets discussed herein.

FIG. 9A shows a support body 910 to which a light source 902 is coupled. For example, the light source could be coupled to support body 910 by clips, fasteners, soldering, or adhesive. FIG. 9A also shows coupling members 912 which are coupled to and extend from support body 912, to couple an end of light director 900 proximate light source 902. In the example of FIG. 9A, coupling members 912 are a plurality of walls positioned around light source 902 (or a single continuous wall which at least partially encircles light source 902). The walls extend from support body 910 beyond light source 902, to form an opening into which an end of light director 900 is received. Light director 900 is secured (permanently or removably) proximate light source 902, for example by friction with coupling members 912, adhesive, clips, or other fasteners. Coupling members 912 also act as light shields or directors when positioned around light source 902 as shown in FIG. 9A. For example, coupling members 912 prevent light from light source 902 from escaping in directions other than into light director 900. Although coupling members 912 are shown in FIG. 9A as having a gap therebetween which is equal around light source 902 and light director 900, in some implementations the gaps are different. For example, light source 902 could be wider than light director 900, and coupling members 912 could be spaced further apart around light source 902 than around light director 900, to appropriately accommodate for the size of each. In another example, light source 902 could be narrower than light director 900, and coupling members 912 could be spaced closer together around light source 902 than around light director 900, to appropriately accommodate for the size of each.

FIG. 9B shows a support body 920 to which a light source 902 is coupled. For example, the light source could be coupled to support body 920 by clips, fasteners, soldering, or adhesive. Support body 920 is similar to support body 910 in FIG. 9A. One difference between the implementation of FIG. 9B and the implementation of FIG. 9A is that in FIG. 9B, light director 900 is coupled to support body 920 by adhesive 914, without additional coupling members like coupling members 912.

FIG. 9C shows a support body 930 to which a light source 902 is coupled. For example, the light source could be coupled to support body 930 by clips, fasteners, soldering, or adhesive. Support body 930 is similar to support body 910 in FIG. 9A. One difference between the implementation of FIG. 9C and the implementation of FIG. 9A is that in FIG. 9C, a plurality of light directors are coupled to support body 930. In particular, two light directors 900a and 900b are shown coupled to support body 930 by coupling members 912 and 913, though additional light directors can be included as appropriate for a given application. Coupling members 912 are similar to those shown in FIG. 9A. Coupling member 913 is shown between light directors 900a and 900b, to secure each light director in place with the cooperation of coupling members 912. Coupling member 913 is optional, but is beneficial for aligning the light directors. In an example, coupling member 913 is omitted, and light redirectors 900a and 900b are secured by a friction fit between coupling members 912. This will result in the secured ends of light directors 900a and 900b being positioned approximately parallel to coupling members 912 (which is approximately perpendicular to the surface of support body 930). However, it is preferable for the secured ends of light directors 900a and 900b to be angled towards the center of light source 902, as is shown in FIG. 9C. This optimizes the amount of light which enters each light director, and optimizes the entry angle of said light to minimize losses. Including coupling member 913 is useful in this regard, as coupling member 913 controls the angle of light directors 900a and 900b to be directed towards a center of light source 902. Each of light directors 900a and 900b can be secured by a friction fit between coupling members 912 and coupling member 913. Further, coupling members 912 and 913 can be an integrally formed structure which defines an respective recess to receive each light director. Other means of securing the light directors is possible, such as clips, fasteners, or adhesive.

Coupling member 913 is one exemplary way to control an angle of light directors coupled to a support body, but other alternatives are possible. For example, each light director could be positioned in the desired angle and secure with adhesive. As another example, each light director could be secured by clips or fasteners which are configured to secure the light director at a desired angle.

As discussed above regarding FIGS. 2A-2D, 3, 4A, and 4B, dispersers on a first support body are optically coupled to at least one light source on a second support body by a plurality of light directors. Coupling mechanisms such as those described with reference to FIGS. 8A-8D are used to couple light directors to the dispersers, and coupling mechanisms such as those discussed with reference to FIGS. 9A and 9B are used to couple the light directors to the at least one light source. Coupling between the dispersers and light directors can be permanent or removable, and coupling between the light source and light directors can be permanent or removable. In this way, a target can be provided as a single permanently assembled unit, or the target can be provided as components to be assembled. For example, a target can be provided as a separate disperser unit (including the dispersers coupled to a first support body), and a light source unit (including the at least one light source coupled to a second support body). A user (such as a surgeon or assistant) can assemble the disperser unit and the light source unit to produce a target. In some implementations, the dispersers can be provided as separate components from the first support body, and a user can assemble the disperser unit by installing the dispersers on the first support body. For example, the dispersers could be installed on the first support body by clips, adhesive, screws, mechanical threads, or other appropriate fasteners.

An advantage to providing a target as separate components to be assembled by a user is that certain components are more easily and repeatably sterilizable, whereas others require more difficult, complex, or expensive sterilization. For example, in hospitals and clinics, steam sterilization is common, such as with an autoclave, but not all materials can withstand the heat and humidity of such steam sterilization. For an element to be "autoclavable", said element should be able to be put through an autoclave procedure, with the result that the element is sterile for future use. That is, an autoclavable material should be sterile and undamaged after an autoclaving procedure. For materials which cannot be autoclaved, other sterilization methods, such as gamma irradiation or ethylene oxide, can be used instead, but these methods may not be available or appropriate for use in hospitals or clinics. Further, certain components may become non-functional before other components (e.g. a battery in the light source unit may die). The separate provision of components allows for the different components to be interchanged or replaced as needed, instead of replacing the whole target. Further still, certain components can be more expensive than others (such as components which require high manufacturing accuracy). It is desirable for such expensive components to be easily sterilizable/autoclavable in a hospital or clinic to avoid replacement, whereas cheaper components are more acceptable as disposable.

In an example, a disperser unit, including a support body and dispersers coupled thereto, is made from materials which are repeatably sterilizable or autoclavable in a hospital or clinic for future sterile use, whereas a light source unit, including a second support body and light sources coupled thereof, may require more sterilization by methods more appropriate at a manufacturing facility. After use, the disperser unit is sterilized for a subsequent procedure, whereas the light source unit is discarded and a new sterile light source unit used for the subsequent procedure. Such new sterile light source units can be provided in packaging which maintains sterility of the light source units, so that the light source units will be sterile when they are removed from the package and assembled with the target. Such an assembly advantageously reduces waste compared to a system where the entire target is replaced for each procedure. In another example, the first support body of the disperser unit is sterilizable, but the dispersers themselves are not. In this case, after a procedure the first support body is sterilized, whereas the dispersers are discarded and new dispersers used for a subsequent procedure.

Even if all of the components are sterilizable in a hospital or clinic, it can still be advantageous for the components to be user-assembled. For example, there may be areas of a target that are difficult to sterilize when fully assembled. After a procedure, the components of the target are disassembled and sterilized, then reassembled for a subsequent procedure.

Figure 10:
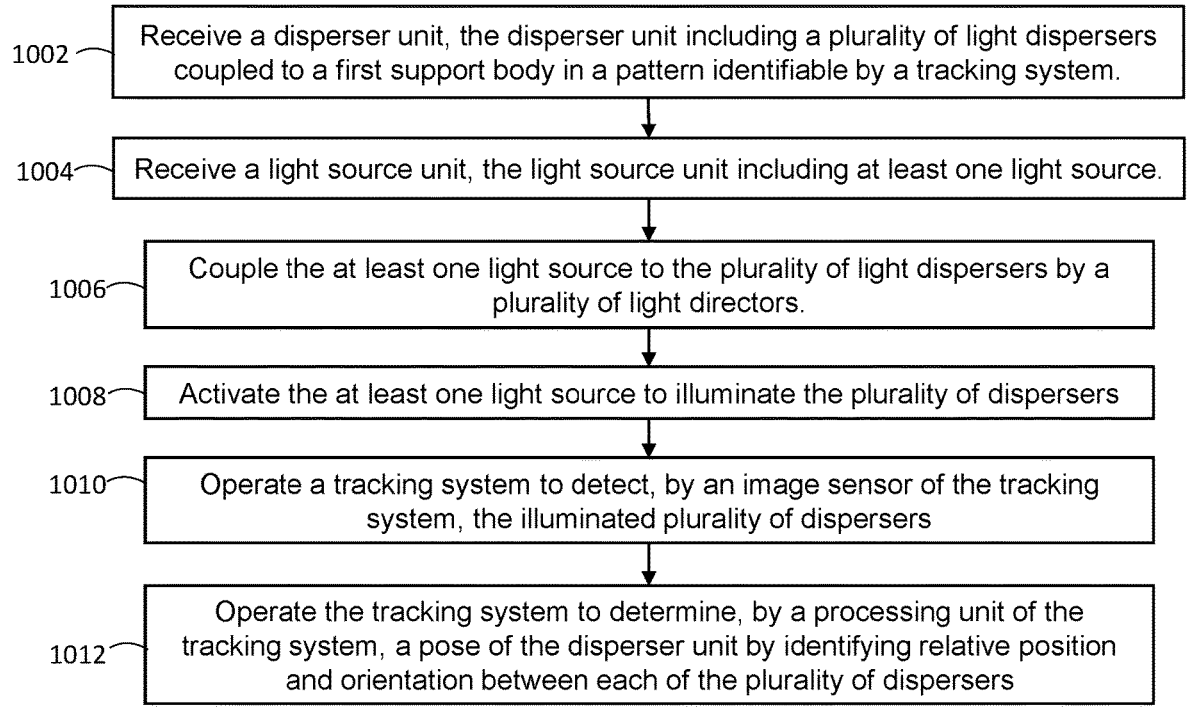
FIG. 10 is a flowchart diagram of a method for assembling and using targets described herein.

FIG. 10 is an exemplary method 1000 for assembling and using any of the targets described above. Method 1000 is shown as including acts 1002, 1004, and 1006, directed towards assembling and/or setting up a target. Method 1000 is also shown as including acts 1008, 1010, and 1012, directed towards tracking the target. Assembling the target and tracking the target can be separately performed by different entities (or could be performed by the same entity), and as such method 1000 could also be considered as a first method including acts 1002, 1004, and 1006, and a second method including acts 1008, 1010, and 1012. The acts of method 1000 could be reordered, acts could be removed, or acts could be added, as appropriate for a given application.

In act 1002, a disperser unit is provided, the disperser unit including a plurality of light dispersers coupled to a first support body in a pattern identifiable by a tracking system. Such a disperser unit could be any of the disperser units described herein, including those described with reference to FIGS. 2A, 2B, 3, 4A, 5, and 6. Further, in implementations where the dispersers are provided separately from the first support body, act 1002 includes assembling the disperser unit by coupling the plurality of dispersers to the first support body.

In act 1004, a light source unit is provided, the light source unit including at least one light source. The light source unit could for example be any of those described with reference to FIG. 2B, 2C, 2D, 3, 4A, 4B, 5, or 6.

In act 1006, the at least one light source is optically coupled to the plurality of light dispersers by a plurality of light directors, such as by any of the mechanisms described with reference to FIGS. 2B, 2C, 2D, 3, 4A, 5, 6, 7A-7G, 8A-8D, 9A, and 9B.

In some implementations, the disperser unit includes the plurality of light directors coupled thereto proximate the plurality of dispersers, and coupling the at least one light source to the plurality of light dispersers comprises coupling the plurality of light directors to the light source unit proximate the at least one light source. Exemplary couplings are discussed with reference to FIGS. 9A and 9B.

In some implementations, the light source unit includes the plurality of light directors coupled thereto proximate the at least one light source, and coupling the at least one light source to the plurality of light dispersers comprises coupling the plurality of light directors to the disperser unit proximate the plurality of dispersers. Exemplary couplings are discussed with reference to FIGS. 8A-8D.

In some implementations, the method includes providing the plurality of light directors separate from the disperser unit and the light source unit. Coupling the at least one light source to the plurality of light dispersers includes coupling a first end of each of the plurality of light directors to the disperser unit proximate the plurality of dispersers, and coupling a second end of the plurality of light directors to the light source unit proximate the at least one light source. Exemplary couplings are discussed with reference to FIGS. 8A-8D and 9A-9B.

In some implementations, the at least one light source comprises a plurality of light sources, and coupling the at least one light source to the plurality of light dispersers comprises coupling each light source of the plurality of light sources to a respective light disperser in the plurality of light dispersers by a respective light director. An exemplary implementation is discussed with reference to FIG. 2D.

In act 1008, the light source unit is activated, so that the plurality of dispersers are illuminated by the at least one light source. In particular, the at least one light source emits light, which is redirected to each disperser, to illuminate each disperser. In implementations where there are a plurality of light sources and dispersers, each disperser is illuminated by a respective light source (if there are an equal amount of light sources and dispersers) or respective light sources (if there are more light sources than dispersers). Activating the light source unit includes, as examples, pressing an on/off switch or button, inserting a battery which completes a power circuit, removing an insulating tab to complete a power circuit, or any other appropriate means of turning the at least one light source on.

In act 1010, a tracking system is operated such that an image sensor of the tracking system detects the illuminated plurality of dispersers. For example, a tracking system can include an image sensor which is sensitive to wavelengths of light emitted by the at least one light source, such that the image sensor will detect the dispersers which are illuminated by the at least one light source.

In act 1012, a tracking system is operated such that a processing unit of the tracking system, determines a pose of the disperser unit (and thus a pose of the target) by identifying relative position and orientation between each disperser of the plurality of light dispersers. In particular, the relative position and orientation of dispersers as viewed by the image sensor can be compared to the pattern identifiable by the tracking system (e.g. pre-defined geometry of the target), to determine how the position and orientation of the dispersers relates to the identifiable pattern (that is, the position and orientation of the dispersers should be some orientation of the pattern in space).

After determining a pose of the target (by determining a pose of the disperser unit), a pose of an anatomy or tool is determined based on the pose of the target.

FIGS. 11A and 11B are side cross-sectional views of another implementation of an active target 1100. Target 1100 includes a first support body 210 having a plurality of dispersers 220, 224, and 226 (and another disperser 222 occluded by disperser 226). First support body 210 and dispersers 220, 222, 224, and 226 can be similar to those of target 200 illustrated in FIGS. 2A and 2B. First support body 210 and the dispersers coupled thereto (dispersers 220, 222, 224, 226) are together referred to as a "disperser unit". One difference between target 200 and target 1100 is that, in target 1100, instead of coupling a light source unit to each disperser with a plurality of light directors, light sources are inserted into the disperser unit to illuminate dispersers directly. FIG. 11A illustrates a second support body 1130 having a stem 1132 coupled thereto, with a light source 1134 positioned at and end of stem 1132 opposite second support body 1130. Similarly, FIG. 11A illustrates a third support body 1140 having a stem 1142 coupled thereto, with a light source 1144 positioned at and end of stem 1142 opposite third support body 1140. Similarly, FIG. 11A illustrates a fourth support body 1150 having a stem 1152 coupled thereto, with a light source 1154 positioned at and end of stem 1152 opposite fourth support body 1150. An additional support body having a stem and light source is provided for assembly with disperser 222, but is occluded in FIGS. 11A and 11B.

The disperser unit and the light sources of target 1100 can be sold, distributed, or provided as separate units, and are assembled as shown in FIG. 11B. In particular, each coupled light source and stem are inserted into a respective recess in first support body 210, with light source 1134 positioned within disperser 220, light source 1144 positioned within disperser 226, and light source 224 positioned within disperser 224 (and with an additional light source positioned within disperser 222). In this way, in use, each light source will directly illuminate a respective disperser.

FIG. 11B shows the light sources being positioned within respective dispersers. However, in alternative implementations the light sources are instead positioned butted against or proximal to respective dispersers to illuminate the dispersers. Further, FIG. 11B shows support bodies 1130, 1140, and 1150 being positioned external to support body 210. In alternative implementations, first support body 210 has recesses therein to accommodate support bodies 1130, 1140, and 1150, such that support bodies 1130, 1140, and 1150 are at least partially inset into first support body 210.

FIGS. 12A and 12B are side views of exemplary light source units which could be used in alternative implementations of target 1100. FIG. 12A illustrates light sources 1134, 1144, and 1154 coupled to respective stems 1132, 1142, and 1152 (and a fourth light source is included, but not illustrated due to occlusion). One difference between the light source unit of FIG. 12A and the light source unit of FIGS. 11A and 11B is that in FIG. 12A, all of the stems are coupled to a common support body 1230, such that all of the light sources can be inserted into first support body 210 together.

FIG. 12B illustrates light sources 1134, 1144, and 1154, to be inserted into support body 210 for use (and a fourth light source is included, but not illustrated due to occlusion). One difference between the light source unit of FIG. 12B and the light source unit of FIGS. 11A and 11B is that in FIG. 12B, no stems are included. Rather, each of the light sources is electrically coupled to support body 1240, which provides power (such as by an included or on-board battery). For example, light source 1134 is coupled to support body 1240 by connector 1242, light source 1144 is coupled to support body 1240 by connector 1244, and light source 1154 is coupled to support body 1240 by connector 1246. Each connector is for example a wire. Each light source is to be individually inserted into a respective recess in support body 210, to illuminate a respective disperser. Support body 1240 is optionally physically coupled to support body 210, to reduce movement of connectors 1242, 1244, and 1246 in use.

In an alternative implementation similar to that shown in FIG. 12B, support body 1240 is a battery or is coupled to a power source, and connectors 1242, 1244, and 1246 comprise flexible PCB. In this way, each of the light sources and the batteries can be manufactured together as a circuit board unit, which can be stored flat but flexed into shape for assembly. Such an implementation advantageously prevents interference, obstruction, or entanglement of loose wires.

The dispersers in FIGS. 11A, 11B, 12A, and 12B are shown as having a circular profile. However, other disperser shapes and types are possible, such as those discussed with reference to FIGS. 7A-7G. Further, each disperser can comprise any of the exemplary caps described with reference to FIGS. 7A-7G, with each said cap being positioned over a respective light source in the plurality of light sources. Said caps can themselves be diffusers, or can be positioned within diffusers, as discussed with reference to FIG. 7F. In an example, with reference to FIG. 11A, light sources 1134, 1144, and 1154 have a cap positioned thereon, such that when the light sources are positioned in the disperser unit, each cap is positioned in the interior volume of a respective disperser.

The dispersers and light source in FIGS. 11A, 11B, 12A, and 12B are shown such that at least one light source and at least one disperser are positioned in a different plane from at least one other light source of the plurality of light sources. However, in some implementations all of the dispersers can be positioned in a common plane, and all of the light sources can be positioned in a common plane.

Similar to as discussed above, certain components of the targets in FIGS. 11A, 11B, 12A, and 12B may be repeatably sterilizable or autoclavable in a hospital or clinical setting, whereas other components may not. In an exemplary implementation, the disperser unit including support body 210 and dispersers 220, 222, 224, and 226 is sterilizable for repeated use, whereas the light source units including support units 1130, 1140, 1150, 1230, and 1240 and the light sources coupled thereto are not. Instead, the light source units are distributed pre-sterilized, and are disposable. In another implementation, support body 210 is sterilizable, but dispersers 220, 222, 224, and 226 are not, with the dispersers being distributed as pre-sterilized disposables.

A method of assembling and using the targets 11A, 11B, 12A, and 12B is similar to method 1000 illustrated in FIG. 10 and discussed above. A difference from method 1000 is in act 1006. Instead of coupling the at least one light source to a plurality of light dispersers by a plurality of light directors, act 1006 is replaced with positioning each light source in an interior volume of or proximate to a respective disperser.

In any of the targets discussed herein, the support bodies to which light sources are coupled can have a battery or power supply, or be coupled to a power source, to provide power to the light sources.

In any of the targets described herein, by virtue of power being supplied to the target (e.g. by a battery or external power supply), additional electrical components can be included in the target itself, to provide additional functionality. FIG. 13 is a side view which illustrates a target 1300 having several additional components.

Target 1300 includes a user input sensor 1302 (e.g., one or more buttons). Such user input sensors are useful to provide additional means for surgical input. In one example, target 1300 is sterilized and positioned in a sterile field during a surgery, whereas other elements of a tracking system are positioned outside of the sterile field. By providing user input mechanisms on target 1300, a surgeon or assistant can provide input to the target directly, without breaking sterility by touching elements outside of the surgical field (such as a user interface of the tracking system). As examples, a user can provide input to user input sensor 1302 to cause target 1300 to output an electrical signal (such as a wireless or wired transmission), to commence a processing operation, or to output an optical signal (such as turning on light sources in target 1300 or causing at least one light source to output encoded data by pulsing).

Target 1300 also includes other sensors 1304, such as an accelerometer, gyroscope, or inclinometer, which provide additional orientation data for the target.

Target 1300 also includes a processing unit 1306, which performs processing of data captured or received by the target. This can include parsing, cropping, or compressing data to be sent to a tracking system, to reduce the size of the transmission. This could also include analyzing data to determine position or orientation of the target. Other exemplary processing can also be performed by processing unit 1306. In some implementations, target 1300 also includes a non-transitory processor-readable storage medium, for storing of data (such as captured, received, or processed data, or instructions for the processing unit 1306).

Target 1300 is also shown as including wireless communication hardware 1308 (e.g., transmitter, receiver, or transceiver). Such communication hardware provides a mechanism for the target to communicate data to a tracking system (such as inputs or measurements from the other sensors 1302 and 1304, or calculations from processing unit 1306), or to receive data from the tracking system. In some implementations, a wired communication interface could be included instead.

Although target 1300 is shown as including all of a user input sensor 1302, other sensors 1304, a processing unit 1306, and wireless communication hardware 1308, all of these components are optional. Some or all of said components could be eliminated, or additional components could be added, as appropriate for a given application.

In implementations where the light source unit includes, carries, or is coupled to a power source, it is preferable for the light source unit to include any additional electrical components, such as user input sensor 1302, other sensors 1304, processing unit 1306, or wireless communication hardware 1308. This enables the electrical components to be connected to the power source within the light source unit. However, it is possible for a disperser unit to carry electrical components, and for the light source unit to couple to the disperser unit such that electrical coupling is provided to power said electrical components (e.g. by electrical contacts between the light source unit and the disperser unit).

In some implementations, at least one light source of any of the targets discussed herein can be configured to output encoded light signals. For example, a light source could flash, pulse, switch on and off, change power output, or change wavelength output in order to transmit data to a tracking system. For example, a light source could pulse according to a binary sequence, and a tracking system can capture and decode this binary sequence, and interpret data indicated therein. In some implementations, any of the targets herein can include an image sensor, which can receive data encoded in sequences of light pulses from other sources (such as other components of a tracking system). A processing unit of the target can receive and decode such pulse sequences to extract the data represented therein.

The targets described herein advantageously are not reliant on external light sources, but instead produce their own dispersed light, which provides improved robustness compared to passive targets which reflect external light. For example, a passive target may be equipped with reflective material. Such material becomes significantly less functional when wet (such as with water, blood, saline solution, antiseptic solution, or other fluids, common in surgical procedures), as the presence of liquid alters the reflective properties of the material (such as reflection angle of light incident thereon), which compromises tracking accuracy. Further, such reflective materials can include retroreflective material, comprising a pattern of glass spheres or balls, or other protruding structures, which tend to capture and retain liquid due to surface tension and capillary action. This makes cleaning of such materials difficult, time consuming, or ineffective, which is problematic during a surgical procedure. The targets described herein, however, produce dispersed light. Even if liquid is present on the dispersers, tracking accuracy will not be significantly compromised. This is because disperse light already includes light travelling evenly in many directions, such that directional changes of the light caused by liquid will generally not be significantly impactful, as the direction of travel of the light is already so varied that the dispersive object will still be visible. This is especially true when the disperser is a diffuser (e.g. made of a light scattering material or having a light scattering surface)

To improve robustness to soiling, an exterior surface of each disperser can optionally be smooth. Liquid will consequently bead off or be easy to clean from the dispersers.

Many of the targets described herein and shown in the Figures include four light sources, four dispersers, and in some cases four light directors. More or less of each of light sources, dispersers, and light directors can be included as appropriate for a given application. In implementations where each disperser is paired or coupled with a respective light director and/or a respective light source, a number of each of said components should be equal. For example, an equal number of dispersers and light directors are included in implementations where a respective light director is provided for each disperser (e.g. target 200 in FIGS. 2A-2D, target 300 in FIG. 3, target 400 in FIG. 4A, target 500 in FIG. 5, and target 600 in FIG. 6). As another example, in implementations where a respective light source is provided for a respective disperser (e.g. light source unit 230b in FIG. 2D, target 400 in FIGS. 4A and 4B, target 1100 in FIGS. 11A and 11B, light source unit 1230 in FIG. 12A, and light source unit 1240 in FIG. 12B), an equal number of light sources and dispersers are provided. As yet another example, in implementations where a respective light source is provided for a respective light director and a respective disperser (e.g. light source unit 230b in FIG. 2D for use in target 200 and 300, target 400 in FIGS. 4A and 4B), an equal number of light sources, light directors, and dispersers are provided.

With reference again to FIG. 1, an optical tracking system is described, in which any of the targets described herein can be used as target 112 or target 114. The optical tracking system further includes an image sensor (image sensor 122 in FIG. 1), and a processing unit (such as a processor in computing device 132 in FIG. 1, or such as processing unit 1306 in target 1300 in FIG. 13). In use, the image sensor captures image data including at least one representation of target 112 or target 114 (including light from dispersers of the target being viewed). Such image data can be a still image, or multiple images, such as a video stream. The captured image data is directed from image sensor 122 to the processing unit (for example by a direct connection or over a network). The processing unit receives the image data, and determines a pose of the target based on the captured image data. In an implementation, the processing unit analyzes the image data to identify and locate the plurality of dispersers represented in the image data. Subsequently, the processing unit compares the position of the plurality of dispersers in the image data to positions of the plurality of dispersers in a model of the target. For example, a CAD or computer model of the target could be accessed by the processing unit, the model having a geometry which matches a known geometry of the target. In other examples, the model could be a simplified model which indicates relative orientation and position of the dispersers, and a key point of the target (such as the tip of an extension from the target, or a centroid of the target). The processor determines a position and orientation (pose) of the real-world target viewed by the image sensor based on the comparison.

In some implementations, the tracking system includes a non-transitory processor-readable storage medium which stores instructions thereon. When executed, said instructions cause the processing unit to perform the actions described above. In other implementations, the processing unit comprises a logic circuit or similar which can perform processing operations without needing to read instructions from a medium.

The various computing devices shown herein can comprise a processing unit (for example a microprocessor, FPGA, ASIC, logic controller, or any other appropriate processing hardware), a storage device (e.g. non-transitory processor-readable storage medium, such as memory, RAM, ROM, magnetic-disk, solid state storage, or any other appropriate storage hardware) storing instructions which when and executed by the processing unit configure the computing device to perform operations for example to provide the functionality and features described herein. Computer program code for carrying out operations may be written in any combination of one or more programming languages, e.g., an object oriented programming language such as Java, Smalltalk, C++ or the like, or a conventional procedural programming language, such as the "C" programming language or similar programming languages.

Any of the computing devices may have communication subsystems to communicate via a network. Any may have a display device and other input and/or output devices.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise", "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers, characteristics, or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

The invention claimed is:

1. A kit for use as a target in optical tracking when assembled, the kit comprising:
   a first support body;
   a plurality of light dispersers to be coupled to the first support body in a pattern identifiable by a tracking system;
   at least one light source to be coupled indirectly to the plurality of light dispersers, the at least one light source to be spatially separated from the plurality of light dispersers when the kit is assembled;
   a plurality of light directors, each light director to direct light from the at least one light source to a respective one of the light dispersers.

2. The kit of claim 1, further comprising a second support body, wherein the at least one light source is affixed to the second support body, and the plurality of light directors are for coupling to the first support body and the second support body.

3. The kit of claim 2, comprising couplings between the plurality of light directors and at least one of the first support body or the second support body to removably couple the plurality of light directors to the first support body or the second support body.

4. The kit of claim 2, comprising a coupling to removably couple the first support body to the second support body.

5. The kit of claim 2, wherein one or both of: the first support body is autoclavable for future sterile use; and the plurality of dispersers are autoclavable for future sterile use.

6. The kit of claim 5, wherein the second support body and the at least one light source affixed thereto are decouplable from the first support body to permit autoclaving the first support body without autoclaving the second support body and the at least one light source.

7. The kit of claim 6, wherein the second support body and the at least one light source are sterile disposable components packaged to maintain sterility prior to assembly.

8. The kit of claim 1, wherein the first support body is adapted to couple the target to an object for optical tracking of the object; and wherein the object is a bone of a patient or a surgical tool.

9. The kit of claim 8, further comprising an extension extending from the first support body, the first support body couplable to the object by a coupling at an end of the extension distal from the first support body.

10. The kit of claim 1, further comprising an extension extending from the first support body; and wherein the target is for optical tracking of an object positioned at an end of the extension distal from the first support body.

11. The kit of claim 1, wherein the plurality of light dispersers includes at least four light dispersers; and the at least one light source includes only one light source, and the plurality of light directors includes an equal number of light directors as there are light dispersers, each light director to direct light from the one light source to a respective one of the light dispersers.

12. The kit of claim 11, wherein the at least one light source includes an equal number of light sources as there are light dispersers, and the plurality of light directors includes an equal number of light directors as there are light dispersers, each light director to direct light from a respective light source to a respective disperser.

13. The kit of claim 1, wherein each disperser comprises one or both of a diverging lens; and a light-scattering material.

14. The kit of claim 1, comprising a plurality of transparent or translucent caps, each cap positioned at an end of a respective light director opposite from the at least one light source.

15. The kit of claim 14, wherein at least one of:
   each cap is dome-shaped or sphere-shaped;
   each cap is mounted to the first support body, and each light director is removably coupled to a respective cap;
   each cap is a disperser in the plurality of dispersers; and
   each cap is configured to be positioned in an interior volume of a respective disperser of the plurality of dispersers.

16. The kit of claim 1, further comprising at least one of: a user input mechanism, wherein the user input mechanism is configured to cause the target to output an electrical or optical signal in response to user input; at least one battery, the at least one light source electrically coupled to the at least one battery; at least one processing unit; and a gyroscope, inclinometer, or an accelerometer.

17. The kit of claim 1, wherein at least one light source of the at least one light source is configured to output encoded light signals.

18. A light source unit for use in an optical tracking target, the target having a plurality of light dispersers coupled to a first support body in a pattern identifiable by a tracking system, the light source unit comprising:

a second support body couplable to the first support body; and a plurality of light sources coupled to the second support body, each light source positioned and oriented to be received in an interior volume of or proximate to a respective light disperser of the target when the second support body is coupled to the first support body.

19. The light source unit of claim 18, wherein the second support body and the plurality of light sources are decouplable from the first support body to permit autoclaving the first support body without autoclaving the second support body and the plurality of light sources.

20. The light source unit of claim 19, wherein the second support body and the plurality of light sources are sterile disposable components packaged to maintain sterility prior to coupling to the first support body.

* * * * *